United States Patent
Zhang et al.

(10) Patent No.: US 12,089,915 B2
(45) Date of Patent: Sep. 17, 2024

(54) METHOD AND SYSTEM FOR PROSTATE MULTI-MODAL MR IMAGE CLASSIFICATION BASED ON FOVEATED RESIDUAL NETWORK

(71) Applicant: HUAZHONG UNIVERSITY OF SCIENCE AND TECHNOLOGY, Hubei (CN)

(72) Inventors: Xuming Zhang, Hubei (CN); Tuo Wang, Hubei (CN)

(73) Assignee: HUAZHONG UNIVERSITY OF SCIENCE AND TECHNOLOGY, Hubei (CN)

( * ) Notice: Subject to any disclaimer, the term of this patent is extended or adjusted under 35 U.S.C. 154(b) by 0 days.

(21) Appl. No.: 18/554,680

(22) PCT Filed: May 10, 2021

(86) PCT No.: PCT/CN2021/092541
§ 371 (c)(1),
(2) Date: Oct. 10, 2023

(87) PCT Pub. No.: WO2022/227108
PCT Pub. Date: Nov. 3, 2022

(65) Prior Publication Data
US 2024/0081648 A1    Mar. 14, 2024

(30) Foreign Application Priority Data
Apr. 25, 2021   (CN) .................. 202110450651.0

(51) Int. Cl.
*A61B 5/055*   (2006.01)
*A61B 5/00*    (2006.01)
(Continued)

(52) U.S. Cl.
CPC .............. *A61B 5/004* (2013.01); *A61B 5/055* (2013.01); *A61B 5/7267* (2013.01); *G06N 3/084* (2013.01);
(Continued)

(58) Field of Classification Search
CPC ......... G06T 7/0012; G06T 2207/20081; G06T 2207/20084; G06T 2207/30081;
(Continued)

(56) References Cited

U.S. PATENT DOCUMENTS 10,311,560 B2 *   6/2019  Sang ........................ G06N 3/08
2010/0329529 A1 * 12/2010  Feldman ........... G06F 18/21375
                                                       382/131
(Continued)

FOREIGN PATENT DOCUMENTS

| CN | 107680053 A | 2/2018 |
| CN | 107886510 A | 4/2018 |

(Continued)

OTHER PUBLICATIONS

Mudassar et al. "FocalNet—Foveal Attention for Post-processing DNN Outputs." International Joint Conference on Neural Networks (IJCNN), Jul. 14, 2019, 8 pages (Year: 2019).*
(Continued)

*Primary Examiner* — Jon Chang
(74) *Attorney, Agent, or Firm* — HSML P. C.

(57) ABSTRACT

The present invention discloses a method and a system for prostate multi-modal MR image classification based on a foveated residual network, the method comprising: replacing convolution kernels of a residual network using blur kernels in a foveation operator, thereby constructing a foveated residual network; training the foveated residual network using prostate multi-modal MR images having category labels, to obtain a trained foveated residual net-
(Continued)

---

Replace convolution kernels of a residual network with blur kernels in a foveation operator, thereby constructing a foveated residual network

↓

Train the foveated residual network by using prostate multi-modal MR images having category labels, so as to obtain a trained foveated residual network

↓

Classify, by using the foveated residual network, a prostate multi-modal MR image to be classified, to obtain a classification result work; and classifying, using the foveated residual network, a prostate multi-modal MR image to be classified, so as to obtain a classification result. In the present invention, a foveation operator is designed based on human visual characteristics, blur kernels of the operator are extracted and used to replace convolution kernels in a residual network, thereby constructing a foveated deep learning network which can extract features that conform to the human visual characteristics, thereby improving the classification accuracy of prostate multi-modal MR images.

9 Claims, 5 Drawing Sheets

(51) Int. Cl.
  *G06N 3/084* (2023.01)
  *G06T 7/00* (2017.01)
  *G06V 10/764* (2022.01)
  *G06V 10/82* (2022.01)
(52) U.S. Cl.
  CPC .. *G06T 7/0012* (2013.01); *G06T 2207/20081* (2013.01); *G06T 2207/20084* (2013.01); *G06T 2207/30081* (2013.01); *G06V 10/764* (2022.01); *G06V 10/82* (2022.01); *G06V 2201/031* (2022.01)
(58) Field of Classification Search
  CPC ........... G06V 10/764; G06V 2201/031; G06V 10/454; G06V 10/82; A61B 5/004; A61B 5/055; A61B 5/7267; A61B 5/0033; G06N 3/084; G06N 3/045; G06N 3/043; G06F 18/2414
  See application file for complete search history.

(56) References Cited

U.S. PATENT DOCUMENTS

2020/0012761 A1* 1/2020 El-Baz ............... G16B 40/30
2021/0225511 A1* 7/2021 Kiraly .................. G06N 3/08

FOREIGN PATENT DOCUMENTS

| CN | 110008992 A | 7/2019 |
| CN | 110930416 A | 3/2020 |
| CN | 111275714 A | 6/2020 |
| CN | 111344801 A | 6/2020 |
| CN | 112508973 A | 3/2021 |
| WO | 2015081079 A1 | 6/2015 |

OTHER PUBLICATIONS

International Search Report and Written Opinion issued in PCT/CN2021/092541, dated Jan. 26, 2022, 13 pages provided, with English translation.

\* cited by examiner

Replace convolution kernels of a residual network with blur kernels in a foveation operator, thereby constructing a foveated residual network Train the foveated residual network by using prostate multi-modal MR images having category labels, so as to obtain a trained foveated residual network Classify, by using the foveated residual network, a prostate multi-modal MR image to be classified, to obtain a classification result

METHOD AND SYSTEM FOR PROSTATE MULTI-MODAL MR IMAGE CLASSIFICATION BASED ON FOVEATED RESIDUAL NETWORK

TECHNICAL FIELD

The present invention belongs to the field of image classification, and more specifically, relates to a method and system for prostate multi-modal MR image classification based on a foveated residual network.

BACKGROUND ART

Prostate cancer is the most common malignancy in the male reproductive system. A report by the American Cancer Society in 2018 indicates that prostate cancer ranks first in new male cases and second for deaths. In recent years, with the significant increase in people's living standards in China and changes in the age structure of the population, prostate cancer morbidity and mortality have risen significantly in China.

MRI can reflect changes in functions of tissues and their visceral organs as well as biochemical metabolic reactions, has advantages such as high resolution imaging of soft tissues, and has important application value in the early diagnosis of prostate cancer. In recent years, new MR imaging techniques are constantly emerging, such as Perfusion Weighted Imaging (PWI), Diffusion Weighted Imaging (DWI), and Diffusion Tensor Imaging (DTI), developed on the basis of MM sequences. Among existing MRI imaging technologies, T2W imaging can display the anatomical structure of the prostate, such that detection of a suspicious lesion can be achieved. However, abnormal conditions such as bleeding, inflammation, and calcification can also result in the presence of low signals in a peripheral zone of the T2W, similar to those exhibited by prostate cancer, which may affect the effect of diagnosing prostate cancer based on the T2W. PWI can precisely locate a lesion with high sensitivity, and also clearly display the degree of invasion of the capsule and seminal vesicles by prostate cancer cells. Among commonly used sequences, T1 Dynamic Contrast Enhancement (DCE) has relatively good contrast agent sensitivity, a relatively high signal-to-noise ratio, sufficient anatomical coverage range, and relatively fast temporal resolution, but requires injection of an exogenous contrast agent, which may cause trauma and tolerance requirements to a patient's body. The Apparent Diffusion Coefficient (ADC) of DWI can reflect the growth and degree of invasion of a tumor. However, the threshold of ADC as a quantitative parameter still needs to be controlled to avoid overdiagnosis. Since the various MM technologies described above have their pros and cons in terms of prostate cancer diagnosis, multiple modalities of MR imaging techniques are typically used in conjunction clinically, so as to avoid missed diagnosis and misdiagnosis, achieving precise diagnosis of prostate cancer.

Currently, an important means of multi-modal MR image classification is Computer-Aided Diagnosis (CAD) technology, which mainly comprises two types. The first type is traditional methods, e.g., feature extraction with manual design, to achieve image classification. Chan et al. first employed a multi-parameter CAD system to diagnose prostate cancer, using line scan diffusion to combine T2 and T2W images with a support vector machine, thereby determining whether prostate cancer is present in a target area of a periprostatic region. Langer et al. performed diagnosis by means of a nonlinear supervised classification algorithm, using a dynamic contrast enhancement image and a pharmacokinetic parameter diagram as additional features of the CAD system for cancer in the prostate peripheral zone, and evaluated the CAD system on the basis of each voxel within a predefined area of interest. Niaf et al. extracted features of a suspected prostate cancer lesion area manually delineated by a physician in T2W, DWI, and DCE modal images and classified them for diagnosis, confirming the results of identifying prostate cancer from a normal area and identifying prostate cancer from a suspicious benign area, but the results are limited to be applicable only in a predefined area of interest in a peripheral area. Overall, these prostate cancer identification methods based on low-order information or manual features, to some extent, are deficient in terms of robustness and generalization ability, due to a lack of efficient mining of inherent high-dimensional information of the images.

Another type of CAD technology automatically extracts features using a deep learning model, thereby obtaining image classification results. Deep learning can automatically extract multi-layer features from inputted medical image data, thus effectively classifying complex data distribution. Convolutional Neural Networks (CNN) which have developed rapidly over the past ten years, are a typical example of a deep learning model, and are widely used in the diagnosis of prostate cancer. Ishioka et al. used a deep neural network to perform assisted diagnosis of patients having a prostate PSA below 20 ng/ml, using T2W and DWI modal images as a training set. Yang Guang of East China Normal University designed a block-based deep convolutional neural network for classifying prostate cancer with multiple parameters; in test data, the value of the Area Under Curve (AUC) of its Receiver Operating Characteristic Curve (ROC) reaches 0.944. Yang Xin of Huazhong University of Science and Technology proposed a multi-modal convolutional neural network for automatically classifying prostate images with multiple parameters, and the classification precision of which is significantly superior to that of the results obtained by traditional machine learning methods.

Overall, the deep learning method has advantages over traditional manual feature extraction methods in terms of prostate image classification. However, the features extracted by the described deep learning models do not necessarily conform to human visual characteristics, which, to some extent, affects the precision of classification methods based on deep learning. Based on this, technical problems exist in the prior art in which it is difficult to extract features conforming to the human visual characteristics and prostate image classification based on deep learning has low precision.

SUMMARY OF THE INVENTION

In view of the above defects or improvement requirements of the prior art, the present invention provides a method and system for prostate multi-modal MR image classification based on a foveated residual network, thereby solving the technical problems in the prior art that it is difficult to extract features conforming to the human visual characteristics and deep learning based prostate image classification has low precision.

In order to achieve the above objective, according to one aspect of the present invention, a method for prostate multi-modal MR image classification based on a foveated residual network is provided, comprising:

Classifying, using a foveated residual network, a prostate multi-modal MR image to be classified, to obtain a classification result;

The construction and training of the foveated residual network comprises:

Replacing convolution kernels of a residual network using blur kernels in a foveation operator, thereby constructing a foveated residual network; and Training the foveated residual network using prostate multi-modal MR images having category labels, so as to obtain a trained foveated residual network.

Furthermore, an optimal perception direction is first determined by means of a derivative of a blur kernel with respect to the perception direction before replacing the convolution kernels of the residual network with the blur kernels in the foveation operator.

Furthermore, the determination of the optimal perception direction comprises:

Generating a total of 180 perception directions from 0° to 179°, from which a plurality of perception directions are randomly selected for initialization, so as to obtain blur kernels and derivatives of the blur kernels with respect to the perception directions; multiplying derivatives of a loss function of the foveated residual network with respect to the blur kernels by the derivatives of the blur kernels with respect to the perception directions to obtain derivatives of the loss function of the foveated residual network with respect to the perception directions, which are back-propagated to obtain updated weights; and using the perception direction corresponding to the blur kernel which is most similar to the updated weight as the optimal perception direction.

Furthermore, the number and dimensions of the blur kernels in the foveation operator are designed to meet requirements regarding the number and dimensions of the convolution kernels in the residual network before replacing the convolution kernels of the residual network with the blur kernels in the foveation operator.

Furthermore, the number of the blur kernels in the foveation operator is:

$$UR=(2\times U\_radius+1)^2$$

Wherein, U_radius is the radius parameter of the blur kernel, and U_radius=4, 6, 8, 11; and UR is the number of the blur kernels.

Furthermore, when the radius parameter of the blur kernels is 4, one blur kernel in the center and 16 blur kernels corresponding to four surrounding corners are removed from 81 blur kernels to obtain 64 blur kernels required for the foveated residual network; when the radius parameter of the blur kernel is 6, one blur kernel in the center and 41 blur kernels corresponding to four surrounding corners are removed from 169 blur kernels to obtain 128 blur kernels required for the foveated residual network; when the radius parameter of the blur kernel is 8, one blur kernel in the center and 32 blur kernels corresponding to four surrounding corners are removed from 289 blur kernels to obtain 256 blur kernels required for the foveated residual network; and when the radius parameter of the blur kernel is 11, one blur kernel in the center and 16 blur kernels corresponding to four surrounding corners are removed from 529 blur kernels to obtain 512 blur kernels required for the foveated residual network.

Furthermore, the dimensions of the blur kernels of the foveated residual network are determined by the following:

Generating an initial blur kernel having dimensions of [2×U_radius+1,2×U_radius+1], and performing average pooling-sampling on the initial blur kernel to determine the dimensions of the blur kernels of the foveated residual network, wherein U_radius is the radius parameter of the blur kernels.

Furthermore, in the average pooling-sampling, a starting point of a pooling window is set to km+b, wherein k and b are linear parameters and m is a row of 3 pooled blur kernels, satisfying the relationship $$\begin{cases} k+b=1 \\ 3k+b+\text{ps}-1=2\times U\_radius+1 \end{cases},$$

that is, it is guaranteed that an upper left starting point of a first pooling window is located at [1,1], and an upper right ending point of a third pooling window is located at [1,2×U_radius+1], wherein ps represents the width of the pooling window.

Furthermore, the pooling windows are adjacent to or overlap with one another, and cannot exceed the boundary of the initial blur kernel.

According to another aspect of the present invention, a system for prostate multi-modal MR image classification based on a foveated residual network is provided, comprising:

A network constructing module configured to replace convolution kernels of a residual network with blur kernels in a foveation operator, thereby constructing a foveated residual network;

A network training module configured to train the foveated residual network using prostate multi-modal MR images having category labels to obtain a trained foveated residual network; and A classifying module configured to classify, using the foveated residual network, a prostate multi-modal MR image to be classified, so as to obtain a classification result.

Furthermore, the network constructing module comprises:

A blur kernel number designing module, which is configured to first configure the number of the blur kernels in the foveation operator to:

$$UR=(2\times U\_radius+1)^2$$

Wherein U_radius is the radius parameter of the blur kernel, and U_radius=4, 6, 8, 11; and UR is the number of the blur kernels; and when the radius parameter of the blur kernels is 4, one blur kernel in the center and 16 blur kernels corresponding to four surrounding corners are removed from 81 blur kernels to obtain 64 blur kernels required for the foveated residual network; when the radius parameter of the blur kernel is 6, one blur kernel in the center and 41 blur kernels corresponding to four surrounding corners are removed from 169 blur kernels to obtain 128 blur kernels required for the foveated residual network; when the radius parameter of the blur kernel is 8, one blur kernel in the center and 32 blur kernels corresponding to four surrounding corners are removed from 289 blur kernels to obtain 256 blur kernels required for the foveated residual network; and when the radius parameter of the blur kernel is 11, one blur kernel in the center and 16 blur kernels corresponding to four surrounding corners are removed from 529 blur kernels to obtain 512 blur kernels required for the foveated residual network;

A blur kernel dimension designing module, which is configured to generate an initial blur kernel having dimensions of [2×U_radius+1,2×U_radius+1], and performing average pooling-sampling on the initial blur kernel to determine the dimensions of the blur kernels of the foveated residual network, wherein U_radius is the radius parameter of the blur kernel; in the average pooling-sampling, a starting point of a pooling window is set to km+b, wherein k and b are linear parameters and m is a row of 3 pooled blur kernels, satisfying the relationship $$\begin{cases} k+b = 1 \\ 3k + b + \text{ps} - 1 = 2 \times \text{U\_radius} + 1 \end{cases},$$

that is, it is guaranteed that an upper left starting point of a first pooling window is located at [1,1], and an upper right ending point of a third pooling window is located at [1,2×U_radius+1], wherein ps represents the width of the pooling window; and the pooling windows are adjacent to or overlap with one another, and cannot exceed the boundary of the initial blur kernel;

A blur kernel direction designing module, which is configured to generate a total of 180 perception directions from 0° to 179°, from which a plurality of perception directions are randomly selected for initialization, so as to obtain blur kernels and derivatives of the blur kernels with respect to the perception directions; to multiply derivatives of a loss function of the foveated residual network with respect to the blur kernels by the derivatives of the blur kernels with respect to the perception directions to obtain derivatives of the loss function of the foveated residual network with respect to the perception directions, which are back-propagated to obtain updated weights; and to use the perception direction corresponding to the blur kernel which is most similar to the updated weight as the optimal perception direction; and A blur kernel replacing module, which is configured to replace the convolution kernels of the residual network with the blur kernels in the foveation operator which are designed in terms of number, dimensions and direction, thereby constructing the foveated residual network.

In general, compared with the prior art, the described technical solutions of the present inventive concept can achieve the following beneficial effects:

(1) The human visual characteristics results from the fovea. At the fovea of the retina, the density of cone cells is very high, and there are almost no rod cells, while the concentration of cone cells decreases as one approaches the periphery of the retina. Therefore, retinal images have different variation characteristics, that is, the definition of the retinal images will be the highest in the middle part of the retina, but as the distance from the center of the retina increases, the images will gradually become blurred. In the present invention, a foveation operator is designed based on the described human visual characteristics, blur kernels of the operator are extracted and used to replace convolution kernels in a deep learning network (i.e., a residual network or ResNet), thereby constructing a foveated deep learning network, which can extract features conforming to the human visual characteristics, thereby improving the precision of classification based on prostate multi-modal MR images.

(2) The perception direction of the blur kernels reflects the direction in which the human eye perceives, at a certain blur kernel size, information regarding an object, and an optimal direction in which the human eye perceives the object is obtained by taking the derivative of the perception direction. The chain rule of a general neural network is to multiply by a continuous function, whereas in the derivation and calculation of blur kernels, the present invention finds that the derivatives of the blur kernels with respect to the perception direction cannot be represented by a deterministic function, as the coefficients thereof vary, so there is no way to directly multiply the derivative into the chain rule using a function. Based on this, in the present invention, a plurality of perception directions are first randomly selected for initialization, so as to obtain blur kernels and derivatives of the blur kernels with respect to the perception directions, then by means of derivatives of a loss function with respect to the perception directions and by passing through back-propagation, an optimal perception direction is finally obtained. The perception directions of the present invention are discrete and not a continuous function. By processing in this way, the convergence rate is much faster, and the gradient will not explode or vanish.

(3) Before the convolution kernels of the residual network are replaced by the blur kernels in the foveation operator, it is necessary to design the number and dimensions of the blur kernels so that the blur kernels meet requirements, enabling the constructed foveated residual network to have a higher classification accuracy. When the number of the blur kernels is designed, the radius parameter of the blur kernels is set to 4, 6, 8 and 11 in order for the number of the blur kernels to be greater than the number of kernels required for the ResNet structure. As such, the number of kernels meeting requirements can be obtained after surplus blur kernels are removed. Average pooling-sampling is employed when designing the dimensions of the blur kernels. A starting point of a pooling window is set and the pooling window is constrained in order to limit the size of the pooling window, so as to obtain a variety of sampling results.

DETAILED DESCRIPTION

In order to make the purpose, technical solution, and advantages of the present invention more clear, the present invention is described in further detail below, with reference to the accompanying drawings and embodiments. It should be appreciated that the specific embodiments described here are used merely to explain the present invention and are not used to define the present invention. In addition, the technical features involved in various embodiments of the present invention described below can be combined with one another as long as they do not constitute a conflict between each other.

Figure 1:
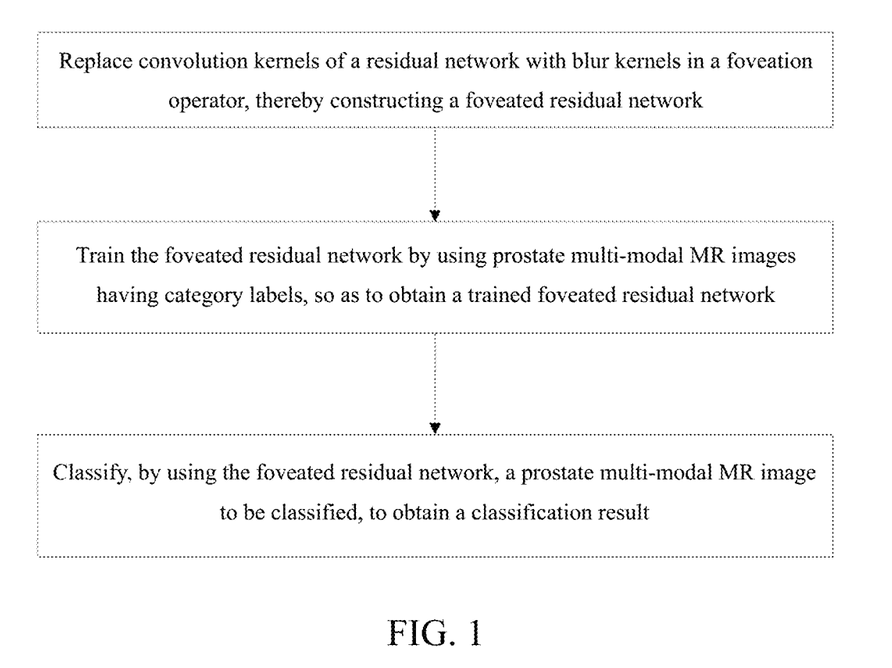
FIG. 1 is a flowchart of a classification method provided in an embodiment of the present invention.

As shown in FIG. 1, a method for prostate multi-modal MR image classification based on a foveated residual network comprises:

Classifying, using a foveated residual network, a prostate multi-modal MR image to be classified, to obtain a classification result;

The construction and training of the foveated residual network comprises:

Replacing convolution kernels of a residual network using blur kernels in a foveation operator, thereby constructing a foveated residual network; and Training the foveated residual network using prostate multi-modal MR images having category labels, so as to obtain a trained foveated residual network.

Furthermore, an optimal perception direction is first determined by means of a derivative of a blur kernel with respect to the perception direction before replacing the convolution kernels of the residual network with the blur kernels in the foveation operator.

Furthermore, the determination of the optimal perception direction comprises:

Generating a total of 180 perception directions from 0° to 179°, from which a plurality of perception directions are randomly selected for initialization, so as to obtain blur kernels and derivatives of the blur kernels with respect to the perception directions; multiplying derivatives of a loss function of the foveated residual network with respect to the blur kernels by the derivatives of the blur kernels with respect to the perception directions to obtain derivatives of the loss function of the foveated residual network with respect to the perception directions, which are back-propagated to obtain updated weights; and using the perception direction corresponding to the blur kernel which is most similar to the updated weight as the optimal perception direction.

The blur kernel b_k and derivative b_k' thereof with respect to the perception direction θ are:

$$b\_k = De^{A_1\cos(2\theta+2Uc)+B_1\sin(2\theta+2Uc)+C_1}, \text{ and}$$

$$b\_k' = (2B_1 D\cos(2\theta+2Uc) - 2A_1 D\sin(2\theta+2Uc))e^{f_1(\theta)},$$

wherein, $$A_1 = \frac{(\rho^2-1)(g^2_{\_1}-g^2_{\_2})}{4\times vs^2 \times \rho},$$

$$B_1 = \frac{(\rho^2-1)g_{\_2}g_{\_1}}{2\times vs^2 \times \rho},$$

$$C_1 = -\frac{(\rho^2+1)(g^2_{\_2}+g^2_{\_1})}{4\times vs^2 \times \rho}, \text{ and}$$

$$D = \frac{1}{2\pi \times vs^2}.$$

ρ represents the degree of focus of the blur kernel, and the present invention uses $$\rho = 2, \text{ and}$$

$f_1(\theta)$ is $A_1\cos(2\theta+2Uc)+B_1\sin(2\theta+2Uc)+C_1$;

$$Uc = a\tan 2\frac{Uc\_2-u\_2}{Uc\_1-u\_1}$$

is the position of the blur kernel in a blur kernel patch; here, $$Uc\_2 = Uc\_1 = \frac{UR+1}{2}, u\_1, u\_2 \in [1, UR],$$

u_1 and u_2 are cycle counts, and Uc_2 and Uc_1 are the sizes of foveation patch; and $g_{\_2}$, $g_{\_1}$ is generated by a grid sampling point function meshgrid, that is, $$[g_{\_2}, g_{\_1}] = \text{meshgrid}\left(\frac{3-u\_2):(UR+2-u\_2)}{5}, \frac{(3-u\_1):(UR+2-u\_1)}{5}\right); \text{ and}$$

$$vs = vsI(u\_1, u\_2], \text{ here, } vsI = \frac{\sqrt{\frac{-2\pi}{\log(e^{-2\pi})}}\times\sqrt{\max(\text{sum}(k\_k))}}{2\sqrt{\pi\times\frac{k\_k}{\text{sum}(k\_k)}}},$$

$$k\_k = 1 - \frac{0.99731774}{(UR-1)^{0.059079081}} \times \overline{l2d}^{0.059079081}$$

is a windowed kernel function, and $l2d_{u\_1\_u\_2} = \sqrt{(-UR+u\_1-1)^2+(-UR+u\_2-1)^2}$.

The derivative of the loss function loss of the residual network with respect to θ may be obtained by multiplying the derivative of loss with respect to the blur kernel with the derivative of the blur kernel with respect to θ:

$$\frac{\partial loss}{\partial \theta} = \frac{\partial loss}{\partial x_{Layer}}\frac{\partial x_{Layer}}{\partial x_{weight}}\frac{\partial x_{weight}}{\partial \theta} = \frac{\partial loss}{\partial x_{weight}} \times b\_k'$$

The coefficients of the derivative formulas cannot be mapped to a unified value by using the same method as they are varying, some being real numbers and some being real matrices, and therefore an approximation method is used to solve the value of θ.

Furthermore, the number and dimensions of the blur kernels in the foveation operator are designed to meet requirements regarding the number and dimensions of the convolution kernels in the residual network before replacing the convolution kernels of the residual network with the blur kernels in the foveation operator.

Furthermore, the number of the blur kernels in the foveation operator is:

$$UR = (2 \times U\_radius + 1)^2$$

wherein, U_radius is the radius parameter of the blur kernel, and U_radius=4, 6, 8, 11; and UR is the number of the blur kernels.

Figure 2A:
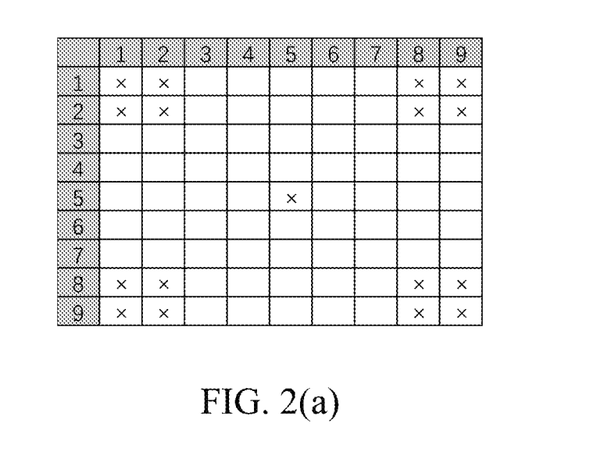
FIG. 2(a) is a design schematic diagram of the number of blur kernels when U_radius=4 provided in the embodiment of the present invention.
Figure 2B:
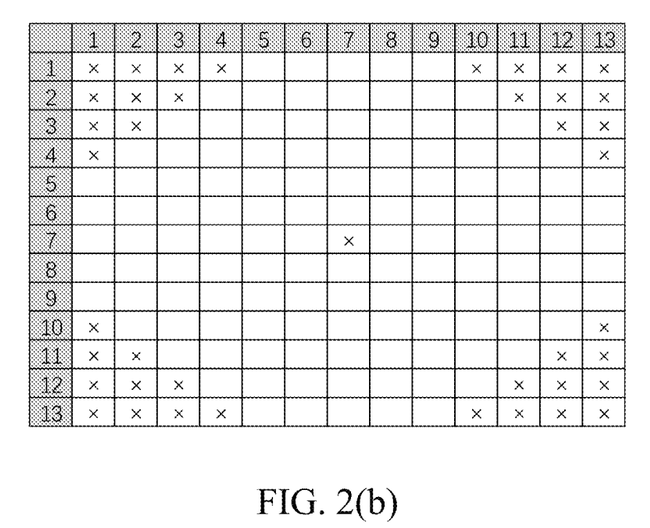
FIG. 2(b) is a design schematic diagram of the number of blur kernels when U_radius=6 provided in the embodiment of the present invention.
Figure 2C:
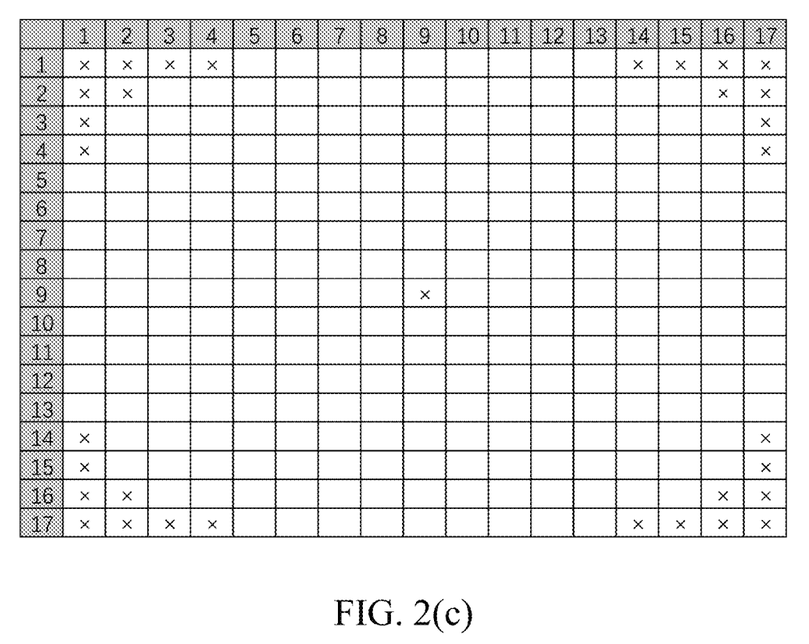
FIG. 2(c) is a design schematic diagram of the number of blur kernels when U_radius=8 provided in the embodiment of the present invention.
Figure 2D:
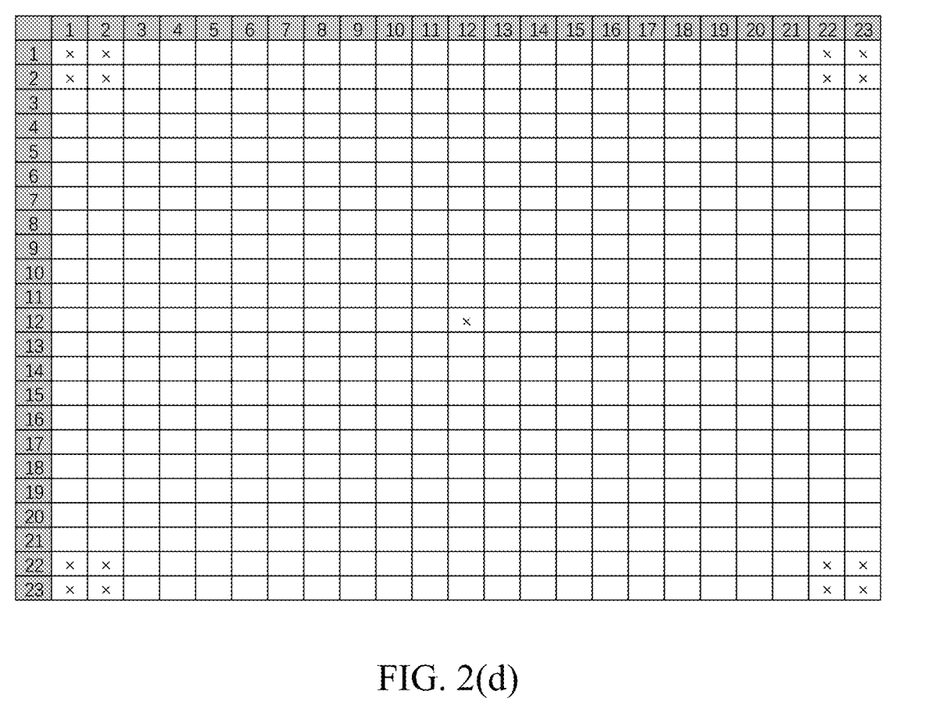
FIG. 2(d) is a design schematic diagram of the number of blur kernels when U_radius=11 provided in the embodiment of the present invention.

As shown in FIG. 2(a), when the radius parameter of the blur kernel is 4, one blur kernel in the center and 16 blur kernels corresponding to four surrounding corners are removed from 81 blur kernels to obtain 64 blur kernels required for the foveated residual network; as shown in FIG. 2(b), when the radius parameter of the blur kernel is 6, one blur kernel in the center and 41 blur kernels corresponding to four surrounding corners are removed from 169 blur kernels to obtain 128 blur kernels required for the foveated residual network; as shown in FIG. 2(c), when the radius parameter of the blur kernel is 8, one blur kernel in the center and 32 blur kernels corresponding to four surrounding corners are removed from 289 blur kernels to obtain 256 blur kernels required for the foveated residual network; and as shown in FIG. 2(d), when the radius parameter of the blur kernel is 11, one blur kernel in the center and 16 blur kernels corresponding to four surrounding corners are removed from 529 blur kernels to obtain 512 blur kernels required for the foveated residual network.

Furthermore, the dimensions of the blur kernels of the foveated residual network is determined by the following:
generating an initial blur kernel having dimensions of [2×U_radius+1,2×U_radius+1], and performing average pooling-sampling on the initial blur kernel to determine the dimensions of the blur kernels of the foveated residual network, wherein U_radius is the radius parameter of the blur kernels.

Furthermore, in the average pooling-sampling, a starting point of a pooling window is set to km+b, wherein, k and b are linear parameters and m is a row of 3 pooled blur kernels, satisfying the relationship $$\begin{cases} k + b = 1 \\ 3k + b + ps - 1 = 2 \times U\_radius + 1 \end{cases}$$

that is, it is guaranteed that an upper left starting point of a first pooling window is located at [1,1], and an upper right ending point of a third pooling window is located at [1,2×U_radius+1], wherein, ps represents the width of the pooling window, and $$k = \frac{2 \times U\_radius + 1 - ps}{2}, \text{ and}$$

$$b = \frac{ps + 1 - 2 \times U\_radius}{2}$$

can be solved.

Furthermore, the pooling windows are adjacent to or overlap with one another, and cannot exceed the boundary of the initial blur kernel. Then:

$$k, b \in Z,$$

-continued $$ps = 2n + 1, n \in Z,$$

$$ps \geq \frac{2 \times U\_radius + 1}{3}, \text{ and}$$

$$ps \leq 2 \times U\_radius - 1.$$

According to constraint conditions, a series of ps values are obtained, and different ps values will result in different sampling effects of an original blur kernel.

Figure 3A:
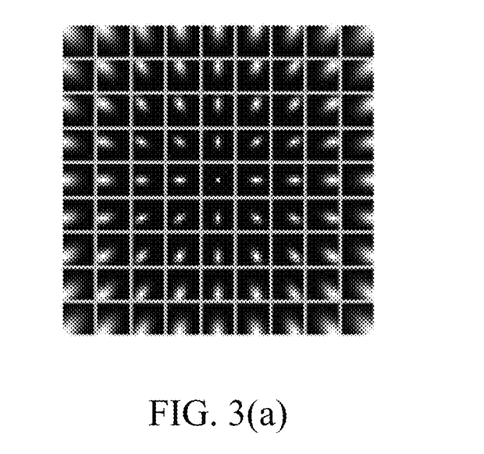
FIG. 3(a) is a schematic diagram of an initial blur kernel which has not undergone pooling-sampling provided in an embodiment of the present invention.
Figure 3B:
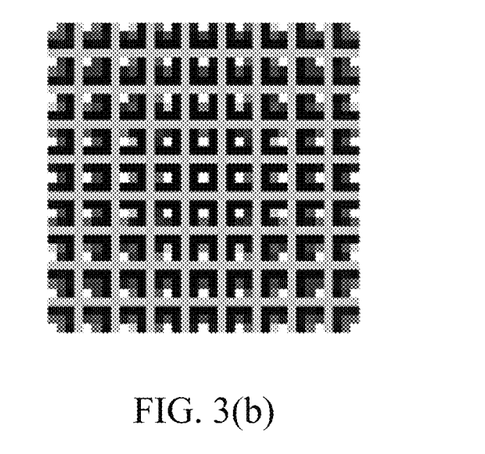
FIG. 3(b) is a schematic diagram of a blur kernel which has undergone pooling-sampling with ps=3 provided in the embodiment of the present invention.
Figure 3C:
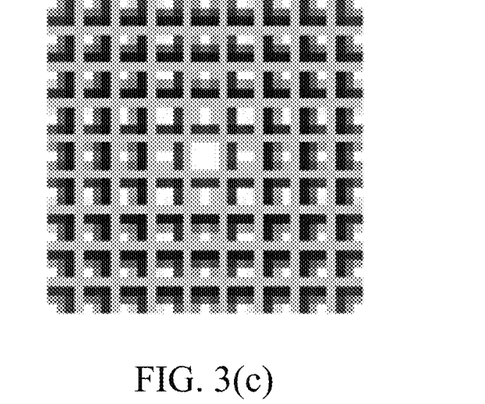
FIG. 3(c) is a schematic diagram of a blur kernel which has undergone pooling-sampling with ps=5 provided in the embodiment of the present invention.
Figure 3D:
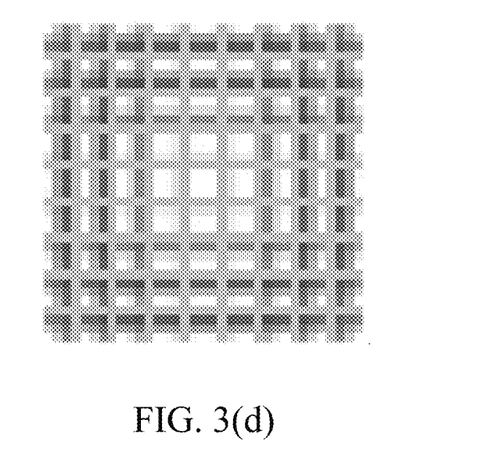
FIG. 3(d) is a schematic diagram of a blur kernel which has undergone pooling-sampling with ps=7 provided in the embodiment of the present invention.

FIG. 3(a) is a schematic diagram of an initial blur kernel which has not undergone pooling-sampling, FIG. 3(b) is a schematic diagram of a blur kernel which has undergone pooling-sampling with ps=3, FIG. 3(c) is a schematic diagram of a blur kernel which has undergone pooling-sampling with ps=5, and FIG. 3(d) is a schematic diagram of a blur kernel which has undergone pooling-sampling with ps=7. It can be clearly seen that, the smaller the ps, the closer to the original blur kernel, and when the smallest ps value is selected, a 3×3 blur kernel closest to the original blur kernel can be obtained.

The blur kernels designed in the present invention for replacement all have dimensions of 3×3, and considered in combination with a smaller data amount and the dimensions of the convolution kernels in ResNet structures, ResNet18 and ResNet34 are selected for replacement, so that it is not required to consider the dimensions of convolution kernels of more layers.

During the training, the training set is the prostate multi-modal MR images having category labels, and in particular:
Step 1-1. Regions of Interest (ROI) comprising a lesion, the raw data of which being T2W, DCE and ADC multi-modal MR images are composed into three-channel multi-modal MR data, which is divided into two types: label 0 for negative, with 250 pictures, and label 1 for positive, with 75 pictures, and has a size of 35×35.
Step 1-2. The data of the ROIs is enhanced using a capsule network-based generative adversarial network, and finally a total of 2600 pictures having label 0 and a total of 2600 pictures having label 1 are generated.
Step 1-3. The data obtained in step 1-2 is divided to obtain a training data set having 1560 pictures for each of label 0 and label 1, a validation data set having 520 pictures for each of label 0 and label 1, and a test data set having 520 pictures for each of label 0 and label 1.
Step 1-4. An original image which has not been enhanced by a generative adversarial network is added into the test set, and finally a total of 720 pictures having label 0 and a total of 582 pictures having label 1 are obtained.

The obtained model (i.e., the foveated residual network) is trained by selecting different training parameters, the model is trained by using the training set and the validation set, an optimal parameter is selected, and the number of training times is deepened.

By training for a different number of times, a model having an optimal classification effect is found.

The obtained optimal model is tested by using the test set, and a model having the best classification effect is selected by means of different test metrics.

Example 1

Step 1. After being input into a network, data that has been prepared has a size of 224×224 and a channel number of 3, and a training data set has 1560 pictures for each of label 0 and label 1, and a validation data set has 520 pictures for each of label 0 and label 1.

Step 2. The number of blur kernels in a foveation operator is designed by removing surplus blur kernels according to the requirements of ResNet structures that the number of kernels are 64, 128, 256, 512, and U_radius=4, 6, 8, 11, such that UR=64, 128, 256, 512.

Step 3. The ps of a pooling window is set to its minimum, and the dimensions of all of the obtained blur kernels is fixed to 3×3.

Step 4. Back-propagation is modified according to the chain rule.

Step 5. A model is trained, and the size of the batch size (BS) is optimized according to the training result, wherein the BS of the ResNet18=32, the BS of the ResNet34=18, the BS of the F-ResNet18=18, and the BS of the F-ResNet34=19.

Step 6. The model is tested, a test set having a total of 720 pictures for label 0 and a total of 582 pictures for label 1, and finally an optimal model is obtained.

Comparative Example 1

Classic ResNet18 and ResNet34 networks are constructed, and trained by using the same data set and loss function as that in the method of the present invention.

Figure 4:
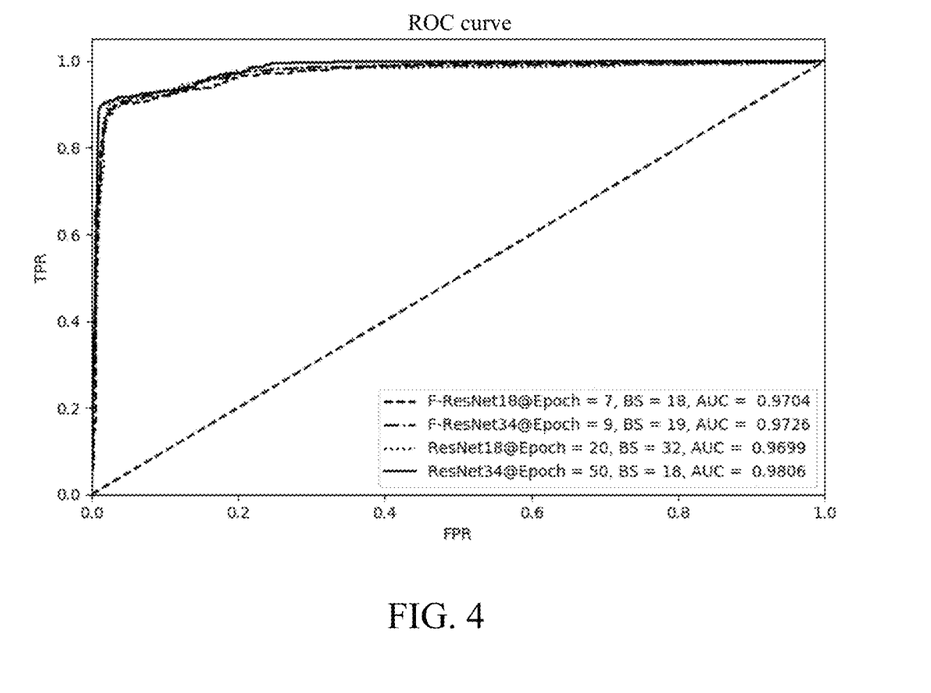
FIG. 4 is a schematic diagram of a ROC curve provided in the embodiment of the present invention.

The results of the present invention and Comparative Example 1 are shown in Table 1 and the schematic diagram of the ROC of FIG. 4.

TABLE 1

| Network Model | Optimal Epoch | ACC | PPV | PRE | SPE | AUC | F1-Score |
|---|---|---|---|---|---|---|---|
| ResNet18 | 20 | 0.9140 | 0.9028 | 0.9393 | 0.8852 | 0.9699 | 0.9207 |
| ResNet34 | 50 | 0.9194 | 0.9125 | 0.9399 | 0.8955 | 0.9806 | 0.9260 |
| F-ResNet18 | 7 | 0.9240 | 0.9417 | 0.9224 | 0.9259 | 0.9704 | 0.9320 |
| F-ResNet34 | 9 | 0.9232 | 0.9278 | 0.9330 | 0.9113 | 0.9726 | 0.9304 |

Comparison of Various Metrics

Assessment metrics used in the present invention include: the area under the ROC curve AUC, accuracy (ACC, all of the results having correct determination/total observed values), precision (PPV, the proportion of the results with a correct prediction in the results having a predicted value of Positive), sensitivity (PRE, the proportion of the results with a correct prediction in the results having a true value of Positive), specificity (SPE, the proportion of the results with a correct prediction in the results having a true value of Negative), and F1-Score (a grade 3 metric, and the closer to 1 the better). At the 20th epoch (number of training times), the ResNet18 reaches the optimal result with the test set having an ACC of 0.9140 and an AUC of 0.9699, and for the F-ResNet18, the test set has an ACC of 0.9240 and an AUC of 0.9704; it may be found that the metrics of the F-ResNet18 of the present invention are better than that of the original ResNet18 structure. The ResNet34 reaches the optimal result at the 50th epoch, with the test set having an ACC of 0.9194 and an AUC of 0.9806, and for the F-ResNet34, the test set has a higher ACC, which is 0.9232, and other metrics are better than that of the results of the original ResNet34, except that the AUC is less than that of the ResNet34 by 0.81%, and the PRE is less than that of the ResNet34 by 0.73%. The foregoing demonstrates that the 18-layer foveated residual network is superior to traditional residual networks in terms of metrics such as classification accuracy, precision, specificity, and F1-Score. The foveated residual network proposed in the present invention can extract image features conforming to the human visual characteristics, providing a new effective means for achieving the precise classification of a prostate cancer multi-modal MR image.

It can be easily understood by a person skilled in the art that the foregoing description is only preferred embodiments of the present invention and is not intended to limit the present invention. Any modifications, identical replacements, improvements and so on that are within the spirit and principle of the present invention should be included in the scope of protection of the present invention.

The invention claimed is:

1. A method for prostate multi-modal MR image classification based on a foveated residual network, the method comprising:
classifying, using a foveated residual network, a prostate multi-modal MR image to be classified, to obtain a classification result;
a construction and training of the foveated residual network comprises:
replacing convolution kernels of a residual network using blur kernels in a foveation operator, thereby constructing a foveated residual network; and
training the foveated residual network using prostate multi-modal MR images having category labels, so as to obtain a trained foveated residual network.

2. The method for prostate multi-modal MR image classification based on a foveated residual network according to claim 1, wherein an optimal perception direction is first determined by means of a derivative of a blur kernel with respect to a perception direction before replacing the convolution kernels of the residual network with the blur kernels in the foveation operator.

3. The method for prostate multi-modal MR image classification based on a foveated residual network according to claim 2, wherein the determination of the optimal perception direction comprises:
generating a total of 180 perception directions from 0° to 179°, from which a plurality of perception directions are randomly selected for initialization, so as to obtain blur kernels and derivatives of the blur kernels with respect to the perception directions; multiplying derivatives of a loss function of the foveated residual network with respect to the blur kernels by the derivatives of the blur kernels with respect to the perception directions to obtain derivatives of the loss function of the foveated residual network with respect to the perception directions, which are back-propagated to obtain an updated weight; and using the perception direction corresponding to the blur kernel which is most similar to the updated weight as the optimal perception direction.

4. The method for prostate multi-modal MR image classification based on a foveated residual network according to claim 1, wherein the number and dimensions of the blur kernels in the foveation operator are designed to meet requirements regarding the number and dimensions of the convolution kernels in the residual network before replacing the convolution kernels of the residual network with the blur kernels in the foveation operator.

5. The method for prostate multi-modal MR image classification based on a foveated residual network according to claim 4, wherein the number of the blur kernels in the foveation operator is:

$$UR=(2\times U\_radius+1)^2$$

wherein, U_radius is the radius parameter of the blur kernel, and U_radius=4, 6, 8, or 11; and UR is the number of the blur kernels.

6. The method for prostate multi-modal MR image classification based on a foveated residual network according to claim 5, wherein when the radius parameter of the blur kernels is 4, one blur kernel in the center and 16 blur kernels corresponding to four surrounding corners are removed from 81 blur kernels to obtain 64 blur kernels required for the foveated residual network; when the radius parameter of the blur kernels is 6, one blur kernel in the center and 41 blur kernels corresponding to four surrounding corners are removed from 169 blur kernels to obtain 128 blur kernels required for the foveated residual network; when the radius parameter of the blur kernels is 8, one blur kernel in the center and 32 blur kernels corresponding to four surrounding corners are removed from 289 blur kernels to obtain 256 blur kernels required for the foveated residual network; and when the radius parameter of the blur kernels is 11, one blur kernel in the center and 16 blur kernels corresponding to four surrounding corners are removed from 529 blur kernels to obtain 512 blur kernels required for the foveated residual network.

7. The method for prostate multi-modal MR image classification based on a foveated residual network according to claim 1, wherein the dimensions of the blur kernels of the foveated residual network are determined by the following:

generating an initial blur kernel having dimensions of [2×U_radius+1,2×U_radius+1], and performing average pooling-sampling on the initial blur kernel to determine the dimensions of the blur kernels of the foveated residual network, U_radius being the radius parameter of the blur kernels.

8. The method for prostate multi-modal MR image classification based on a foveated residual network according to claim 7, wherein in the average pooling-sampling, a starting point of a pooling window is set to km+b, wherein k and b are linear parameters and m is a row of 3 pooled blur kernels satisfying the relationship $$\begin{cases} k+b=1 \\ 3k+b+\text{ps}-1=2\times U\_radius+1 \end{cases},$$

that is, it is guaranteed that an upper left starting point of a first pooling window is located at [1,1], and an upper right ending point of a third pooling window is located at [1, 2×U_radius+1], wherein ps represents the width of the pooling window.

9. The method for prostate multi-modal MR image classification based on a foveated residual network according to claim 8, wherein the pooling windows are adjacent to or overlap with one another, and cannot exceed the boundary of the initial blur kernel.

\* \* \* \* \*